(12) United States Patent
Houser et al.

(10) Patent No.: US 7,078,548 B2
(45) Date of Patent: *Jul. 18, 2006

(54) HYPERBRANCHED CHEMOSELECTIVE SILICON-BASED POLYMERS FOR CHEMICAL SENSOR APPLICATIONS

(75) Inventors: Eric J. Houser, Ocean View, NJ (US); Robert A. McGill, Lorton, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/091,024

(22) Filed: Mar. 6, 2002

(65) Prior Publication Data

US 2003/0168355 A1    Sep. 11, 2003

(51) Int. Cl.
*C07F 7/08* (2006.01)
*C07F 7/12* (2006.01)

(52) U.S. Cl. ..................... 556/431; 556/435
(58) Field of Classification Search ............ 556/431, 556/435
See application file for complete search history.

(56) References Cited

U.S. PATENT DOCUMENTS

| | | | |
|---|---|---|---|
| 6,001,945 A | 12/1999 | Decker et al. | |
| 6,114,489 A | 9/2000 | Vicari et al. | |
| 6,140,525 A | 10/2000 | Okawa et al. | |
| 6,617,040 B1 * | 9/2003 | Houser et al. | 428/447 |
| 6,630,560 B1 * | 10/2003 | McGill et al. | 528/25 |
| 6,660,230 B1 * | 12/2003 | McGill et al. | 422/82.13 |

OTHER PUBLICATIONS

Database CAPLUS on STN, Acc. No. 1975:171159, Abel et al, Journal of Organometallic Chemistry (1975), 84(2), p. 199-229 (abstract).*
Kim et al, End-Capped AB3-Type Hyperbranched Carbosilane Macromolecules, J. Polymer Science, vol. 39, pp. 3287-3293 (2001).
Yao et al, Synthesis of an Organosilicon Hyperbranched Oligomer Containing Alkenyl and Silyl Hydride Groups, J. Polymer Science, vol. 37, pp. 3778-3784, (1999).
Whitmarsh et al, Synthesis and Structure of a Highly Branched Polycarbosilane Derived from (Chloromethyl) trichlorosilane, Organometllics, 1991, vol. 10., pp. 1336-1344.
Uhlig, Convenient Approach to Novel Functional Substituted and Branched Poly (silylenemethylenes), J. Polymer Science, vol. 36, (1998), pp. 725-735.

* cited by examiner

*Primary Examiner*—Brian Davis
(74) *Attorney, Agent, or Firm*—John J. Karasek; Stephen T. Hunnius

(57) ABSTRACT

The invention provides a device for selective molecular recognition, the device comprising a sensing portion, wherein said sensing portion includes a substrate having coated thereon a layer comprising a hyperbranched compound having:
(1) a polymer backbone portion that is at least partly randomly branched;
(2) at least one pendant group extending from the polymer backbone portion; and
(3) at least one halogen substituted alcohol or phenol group substituted at the pendant group(s) of the polymer backbone portion.

The compound of the invention preferably has the general formula:

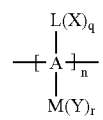

wherein A is the hyperbranched backbone portion of the polymer;
L and M are independently selected pendant groups of said polymer backbone;
X and Y are independently selected halogen substituted alcohol or phenol groups;
q and r are independently selected and at least 1; and
n is at least 3.
The device is used to detect the molecules of a hydrogen bond accepting vapor such as organophosphorus or nitroaromatic species.

3 Claims, 2 Drawing Sheets

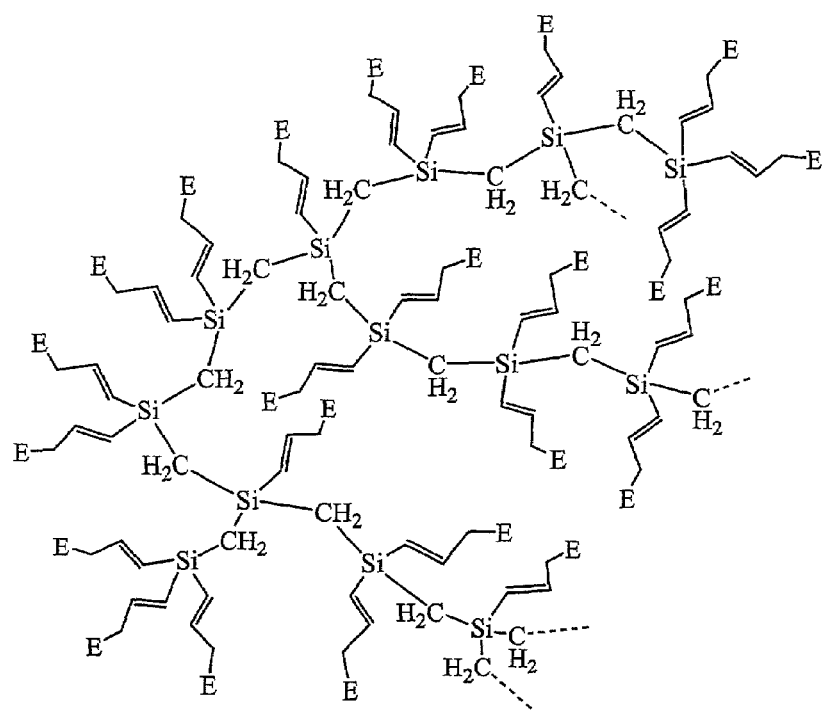
E = -C(CF$_3$)$_2$OH
Figure 1. Hyperbranched polycarbosilane with fluoroalcohol functionalized allyl groups.

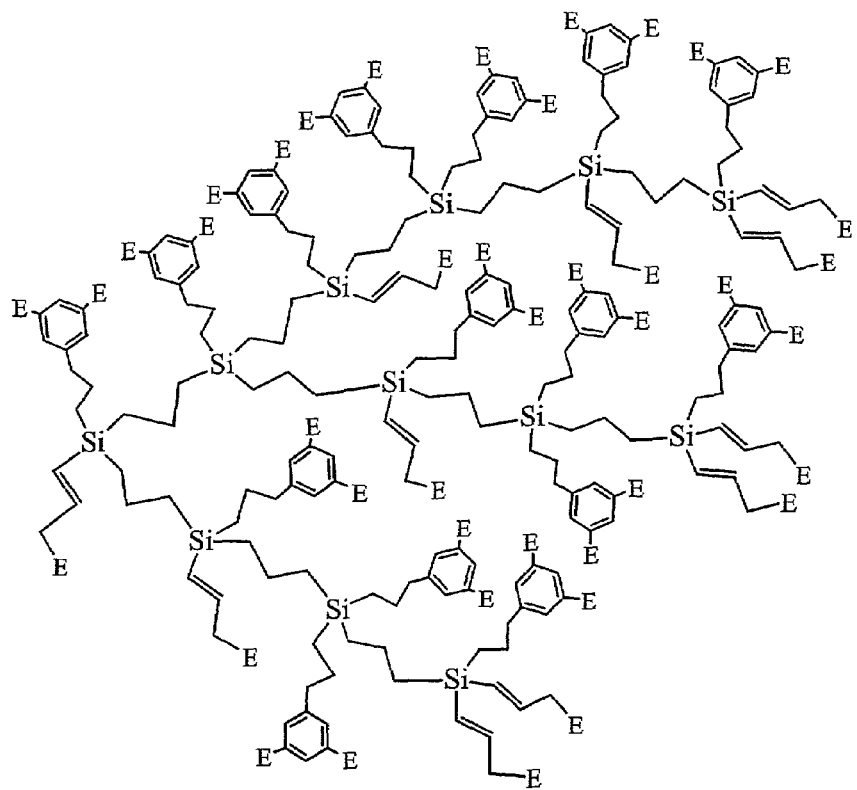
E = -C(CF$_3$)$_2$OH
Figure 2. Hyperbranched polycarbosilane with fluoroalcohol functionalized phenyl and allyl groups.

HYPERBRANCHED CHEMOSELECTIVE SILICON-BASED POLYMERS FOR CHEMICAL SENSOR APPLICATIONS

BACKGROUND OF THE INVENTION

1. Field of the Invention

The present invention relates to the detection of noxious chemical species by means of chemoselective hyperbranched polymeric compounds. More particularly, the invention relates to the detection of toxic or explosive chemical vapors, such as chemical agents or nitro-substituted species, respectively, by sorbent materials comprising chemoselective hyperbranched polymeric molecules.

2. Description of Related Art

Determining and/or monitoring the presence of certain chemical species within an environment, e.g., pollutants, toxic substances and other predetermined compounds, is becoming of increasing importance with respect to such fields as health, environmental protection, resource conservation, and chemical processes. Devices for the molecular recognition of noxious species or other analytes typically include (1) a substrate and (2) a molecular recognition coating upon the substrate. These devices may be used, for example, in chemical vapor sensing or the selective separation of gases by gas chromatography. Small molecular recognition devices are described in Grate et al., *Sensors and Actuators B*, 3, 85–111 (1991) and Grate et al., *Analytical Chemistry*, Vol. 65, No. 14, Jul. 15, 1993, both of which are incorporated herein by reference.

Frequently, the substrate is a piezoelectric material or a waveguide, which can detect small changes in mass. One illustrative example of a device relying upon molecular recognition as a surface is known as a surface acoustic wave (SAW) sensor. SAW devices function by generating mechanical surface waves on a thin slab of a piezoelectric material, such as quartz, that oscillates at a characteristic resonant frequency when placed in a feedback circuit with a radio frequency amplifier. The oscillator frequency is measurably altered by small changes in mass and/or elastic modulus at the surface of the SAW device.

SAW devices can be adapted to a variety of gas-phase analytical problems by designing or selecting specific coatings for particular applications. The use of chemoselective polymers for chemical sensor application is well established as a way to increase the sensitivity and selectivity of a chemical sensor with respect to specific classes or types of analytes. Typically, a chemoselective polymer is designed to contain functional groups that can interact preferentially with the target analyte through dipole-dipole, Van der Waal's, or hydrogen bonding forces. For example, strong hydrogen bond donating characteristics are important for the detection of species that are hydrogen bond acceptors, such as toxic organophosphorus compounds. Increasing the density of hydrogen bond acidic binding sites in the coating of a sensor results in an increase in sensitivity.

Chemoselective films or coatings used with chemical sensors have been described by McGill et al. in *Chemtech*, Vol. 24, No. 9, 27–37 (1994). The materials used as the chemically active, selectively absorbent of a molecular recognition device have often been polymers, as described in Hansani in *Polymer Films in Sensor Applications* (Technomic, Lancaster, Pa. 1995). For example, Ting et al. investigated polystyrene substituted with hexafluoroisopropanol (HFIP) groups for its compatibility with other polymers in *Journal of Polymer Science: Polymer Letters Edition*, Vol. 18, 201–209 (1980) Later, Chang et al. and Barlow et al. investigated a similar material for its use as a sorbent for organophosphorus vapors, and examined its behavior on a bulk quartz crystal monitor device in *Polymer Engineering and Science*, Vol. 27, No. 10, 693–702 and 703–15 (1987). Snow et al. (*NRL Letter Report*, 6120–884A) and Sprague et al. (*Proceedings of the 1987 U.S. Army Chemical Research Development and Engineering Center Scientific Conference on Chemical Defense Research*, page 1241) reported making materials containing HFIP that were based on polystyrene and poly(isoprene) polymer backbones, where the HFIP provided strong hydrogen bond acidic properties. These materials were used as coatings on molecular recognition devices, such as SAW sensors, and showed high sensitivity for organophosphorus vapors. However, both the parent polymers and the HFIP-containing materials were glassy or crystalline at room temperature. Because vapor diffusion may be retarded in glassy or crystalline materials, the sensors produced were slow to respond and recover. Further, these are polymeric materials and, like all polymers, they can vary significantly from batch to batch in precise composition, purity and yield. Additional information is reported in *Polym. Eng. Sci.*, 27, 693 and 703–715 (1987).

Vicari et al., U.S. Pat. No. 6,114,489, issued Sep. 5, 2000, discloses reactive hyperbranched polymers containing terminal hydroxy, carboxy, epoxy, and isocyanate groups. The compounds are useful as components in powder coating compositions for the formation of hard, impact resistant films. Examples of the preferred hyperbranched polyesters are those formed from α,α-bis(hydroxymethyl)-propionic acid. The backbone of these hyperbranched polymers are composed of polyester units.

Okawa et al., U.S. Pat. No. 6,140,525 issued Oct. 31, 2000, discloses a class of hyperbranched polymers that are prepared by contacting macromonomers that have both silicon hydride and unsaturated organic terminal groups with group VIII metal catalysts. The hyperbranched polymers are useful as surfactants, gelling agents, drug delivery systems, and polymeric absorbents. The hyperbranched polymer backbones are comprised of a combination of siloxane and carbosilane segments. Examples of preferred macro-monomers include $(HSi(CH_3)_2O)_2Si(CH_3)OSi(CH_3)_2(CH_2)_2(Si(CH_3)_2O)_nSi(CH_3)_2CH=CH_2$, where n is 10 to 100

Decker et al., U.S. Pat. No. 6,001,945, issued Dec. 14, 2001, discloses hyperbranched polymers containing silicon atoms and a method of making these materials. The exchange (condensation) reaction that forms the hyperbranched polymers results in the elimination of an alcohol by-product and the formation of hyperbranched polymer backbones comprised of siloxane linkages.

The inventors have now discovered a class of hyperbranched molecules that can be used to produce hydrogen bond acidic coatings for chemical sensor applications. Using the hyperbranched molecules that are highly functionalized results in significant sensitivity improvements. Further, the chemoselective hyperbranched molecules of the present invention exhibit, not only improved sensitivity to organophosphorus species, but also high selectivity and sensitivity toward nitro-substituted chemical vapors, and are thus also useful for detecting the presence of explosives. Conventional explosives, such as trinitrotoluene (TNT), hexahydro-1,3,5-trinitro-1,3,5-triazine (RDX), and octahydro-1,3,5-trinitro-1,3,5,7-tetrazocine (HMX), may be contained in unexploded munitions, e.g., buried below the surface of the ground. Such munitions exude or leak vapors of the explosive. These vapors are typically concentrated in the surrounding soil and then migrate to the surface where they can be detected by the compounds, devices and methods of the invention.

SUMMARY OF THE INVENTION

According to a first aspect of the present invention, there is provided a hyperbranched polymeric compound having; (1) a polymer backbone portion that is at least partly randomly branched; (2) at least one pendant group extending from the polymer backbone portion; (3) and at least one halogen substituted alcohol or phenol group substituted at the pendant group(s) of the polymer backbone portion.

According to a second aspect of the invention, there is provided a device for selective molecular detection, the device comprising a sensing portion, wherein the sensing portion includes a substrate having coated thereon a layer, the layer comprising the hyperbranched compound of the invention.

According to another aspect of the invention, there is provided a method of detecting a hydrogen bond accepting vapor, such as a nitroaromatic vapor, comprising the steps of:
(a) contacting the molecules of such a vapor with the sensing portion of the device of the invention;
(b) collecting the molecules in the layer of the device, the molecules altering a specific physical property of the layer; and
(c) detecting the amount of change with respect to the physical property from before the contacting step (a) and after the collecting step (b).

According to yet another aspect of the invention, there is provided a solution for preparing a chemical vapor sensor comprising (a) an amount of the hyperbranched compound of the invention effective to enhance the sensitivity of the sensor to hydrogen bond accepting vapors such as chemical agents or nitroaromatic compounds and (b) a solvent for the hyperbranched compound.

BRIEF DESCRIPTION OF THE DRAWINGS

FIG. 1 shows an example of a hyperbranched compound of the invention, here, a hyperbranched polycarbosilane with fluoroalcohol functionalized allyl groups.

FIG. 2 shows another example of a hyperbranched compound of the invention, here, a hyperbranched polycarbosilane with fluoroalcohol functionalized phenyl and allyl groups.

DETAILED DESCRIPTION OF THE INVENTION

The hyperbranched molecules of the invention are polymeric molecular constructions having a randomly branched backbone portion with attached pendant groups. The randomly branched backbone portion of the molecule may be composed of linear, branched, and dendritic units, which may themselves be further branched, forming the backbone portion of the hyperbranched polymer molecule. The detailed chemical structure of the hyperbranched backbone may dominate certain polymer physical properties. Hyperbranched polymers may be distinguished from dendritic, branched, and linear polymers in that:
(a) The degree and distribution of branching in a hyperbranched polymer is variable and, therefore, the molecular weight of the hyperbranched materials usually occurs over a broad distribution while a dendrimer has a precise structure and molecular weight;
(b) The chemical synthesis of a hyperbranched polymer may be carried out in a single step from the starting monomer, whereas the synthesis of a dendritic polymer requires a multistep synthetic procedure;
(c) Linear polymers are not branched; and
(d) Branched polymers are branched in a regular fashion whereas hyperbranched polymers are branched in a random fashion.

Although not bound by theory, it is believed that the hyperbranched morphology offers advantages over linear macromolecules with the same or similar repeating units because the randomly branched structure imposes particular physical properties such as reduced polymer chain entanglement, lower glass transition and melting temperatures and increased availability of terminal functional groups. These constraints, often including steric crowding, inhibit even very long chains from packing in their thermodynamically preferred conformations for crystallization, and thereby lower their melting points due to entropic factors. The random variation in structure that occurs with hyperbranched materials is also a contributing factor to the bulk properties of these materials. By controlling the structure of the hyperbranched polymer, for example, with suitable ratios of branching arm length to average branch multiplicity, the free volume available to the chain ends can be made relatively large. In this case, a large free volume at the chain ends may facilitate arm segmental motion, although this effect is often negated by steric crowding at the terminal groups.

The compound of the invention is a hyperbranched polymeric compound having; (1) a polymer backbone portion that is at least partly randomly branched; (2) at least one pendant group extending from the polymer backbone portion; (3) and at least one halogen substituted alcohol or phenol group substituted at the pendant group(s) of the polymer backbone portion. The compound may be entirely organic or organometallic in composition. Preferred compounds can be represented by the general formula:

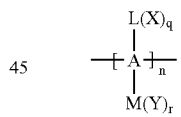

wherein A is the hyperbranched backbone portion of the polymer;

L and M are independently selected pendant groups of the polymer backbone;

X and Y are independently selected halogen substituted alcohol or phenol groups;

q and r are independently selected and at least 1, preferably ranging from 1 to about 10; and n is at least 3, preferably ranging from 20 to 100,000.

A, the hyperbranched backbone portion of the compound, may be composed of repeating units consisting of a single atom such as a carbon or silicon atom; a hydrocarbon moiety; an organometallic fragment or cluster; or a silicon based moiety such as a siloxane, carbosilane, or silylene moiety; or a combination thereof. Examples of useful "A" backbone repeat units include $\{Si-(-Z)_x\}$, $\{C-(-Z)_x\}$, $Fe(-C_5H_4Z-)_2$, $C_6H_n(-Z)_{6-n}$, and the like, wherein Z is a hydrocarbon, silylene, carbosilane, siloxane, or carbosiloxane fragment of 1 to 20 atoms in length, including but not limited to alkylene, alkenylene, alkynylene, cycloalkylene, cycloalkenylene, arylene, or heterocyclene. Preferably, however, A is {Si-(alkylene-)}, {Si-(arylene-)}, or {Si-(alkenylene-)}. Most preferably, A is {Si[(CH$_2$)$_x$]} wherein x is 1 to 3.

L and M in the above formula are independently selected pendant groups that extend from the hyperbranched backbone portion of the compound. L or M may be saturated or unsaturated. By "unsaturated" is meant any site of unsaturation, such as, for example, a double or triple bond or an aromatic ring. L or M may be entirely hydrocarbon or may contain one or more heteroatoms, such as, for example, Si, N, O, S, F, Cl, Br and the like, and may contain further branching entities. For example, L or M may independently be alkylene, alkenylene, alkynylene, arylene, alkylene-arylene, alkenylene-arylene, alkynylene-arylene, —C-(alkenylene)$_3$, —Si-(alkenylene-)$_3$, —N-(alkenylene-)$_2$, or —SiO-(alkenylene-)$_3$, where alkenylene is as defined above; —C-[alkylene-Si-(alkenylene)$_3$]$_3$, —Si-[alkylene-C-(alkenylene)$_3$]$_3$, —Si-[alkylene-Si-(alkenylene)$_3$]$_3$, —SiO-[alkylene-Si-(alkenylene)$_3$]$_3$, —CO-[alkylene-Si-(alkenylene)$_3$]$_3$, —Si-[alkylene-N-(alkenylene)$_2$]$_3$, where alkylene and alkenylene are defined as above; —C-(cycloalkenylene-)$_3$, —Si-(cycloalkenylene-)$_3$, and CON-(cycloalkenylene-)$_3$, where cycloalkenylene is defined as above; —C-[cycloalkylene-Si-(alkenylene)$_3$]$_3$, —Si-[cycloalkylene-C-(alkenylene)$_3$]$_3$, —Si-[cycloalkylene-Si-(alkenylene)$_3$]$_3$, —SiO-[cycloalkylene-Si-(alkenylene)$_3$]$_3$, —CO-[cycloalkylene-Si-(alkenylene)$_3$]$_3$, —Si-[cycloalkylene-N-(alkenylene)$_2$]$_3$, where cycloalkylene and alkenylene are defined as above; —C-(arylene-)$_3$, —Si-(arylene-)$_3$, and —SiO-(arylene-)$_3$, where arylene is defined as above; —C-(heterocyclene-)$_3$, —Si-(heterocyclene-)$_3$, and —SiO-(heterocyclene-)$_3$, where heterocyclene is as defined above; —C-[alkylene-Si-(alkylene-arylene)$_3$]$_3$, —Si-[alkylene-C-(alkylene-arylene)$_3$]$_3$, —Si-[alkylene-Si-(alkylene-arylene)$_3$]$_3$, —SiO-[alkylene-Si-(alkylene-arylene)$_3$]$_3$, —CO-[alkylene-Si-(alkylene-arylene)$_3$]$_3$, —Si-[alkylene-N-(alkylene-arylene)$_2$]$_3$, where alkylene or arylene are defined as above.

Preferably, however, L and M are independently an alkenylene, aklylene-arylene, alkeneylene-arylene, -[alkylene-Si-(alkenylene)$_n$]$_3$ or an -[alkylene-Si-(alkylene-arylene)$_3$]$_3$ group. Even more preferably, L and M are independently —(CH$_2$)$_m$—, —(CH=CH—CH$_2$)—, —[(CH$_2$)$_m$C$_6$H$_4$]—, —[(CH$_2$)$_m$—Si—(CH=CH—CH$_2$—)$_3$]$_3$ or —Si—{(CH$_2$)$_m$—Si—[—(CH$_2$)$_n$—C$_6$H$_4$—]$_3$}$_3$ wherein m and n are independently 1 to 6.

The novel compounds of the invention are strongly hydrogen bond donating. They are useful in a variety of applications, especially as a coating material on chemical sensors. They are very sensitive for hydrogen bond accepting vapors such as organophosphorus and nitro-substituted compounds such as a those in a great number of well-known toxic and explosive materials, respectively.

The compounds of the invention can be synthesized by reacting hexafluoroacetone with the parent hyperbranched molecule, comprising a hyperbranched backbone A and a number of pendant unsaturated groups, taking advantage of the reactivity of perfluoroketones with terminally unsaturated groups, as described by Urry et al., *J. Org. Chem.*, 1968, 33, 2302–2310, hereby incorporated by reference. Alternatively, the compounds of the invention can be synthesized by reacting hexafluoroacetone with the parent hyperbranched molecule, comprising a hyperbranched backbone A and a number of pendant groups containing metalated sites, followed by protonation, as described by Barbarich er al., *J. Am. Chem. Soc.*, 1999, 121, 4280–4281, hereby incorporated by reference. Two such hyperbranched compounds of the invention are shown in FIGS. 1 and 2. Using known methods (see, for example, Whitmarsh, C. K., Interrante, L. V. *Organometallics*, 1991, 10, 1336–1344; Uhlig, W. *J. Polym. Sci., Part A: Polym. Chem.*, 1998, 36, 725–735 and Koopman, F., Frey, H. *Macromolecules* 1996, 29, 3701–3706.) these compounds are typically synthesized in moderate to high yield.

Once synthesized, these functionalized hyperbranched compounds can be coated to a controlled film thickness on a substrate, either alone or mixed with a solvent or similarly functionalized molecule. Useful substrates include planar chemical sensors, such as surface acoustic wave (SAW) substrates; silica optical fibers; microcantilevers and other MEMS devices, and the interior surfaces of silica capillaries. The substrate chosen is based on the sensing mechanism being used.

The principle of operation of an acoustic wave device transducer involves the production of an acoustic wave that is generated on the surface or through the bulk of a substrate material and allowed to propagate. To generate an acoustic wave typically requires a piezoelectric material. Applying a time varying electric field to the piezoelectric material will cause a synchronous mechanical deformation of the substrate with a coincident generation of an acoustic wave in the material. The time varying electric field is generated in the surface by applying a time varying electrical field through one or more electrodes, which are connected to the piezoelectric material via one or more metal wire bonds and to an electrical circuit. Another electrode or electrodes receives the wave at a distance from the first electrode or electrodes. The second electrode or electrodes is also connected via metal wire bonds to the electrical circuit and the piezoelectric material. Such devices are operable in a frequency range of about 2 kilohertz to 10 gigahertz, preferably from about 0.2 megahertz to about 2 gigahertz and, more preferably, in the range of between about 200 to 1000 megahertz.

For piezoelectric sensors, piezoelectric substrates well-known in the art, such as ST-cut quartz, are useful in accordance with the invention. In addition to quartz crystals, piezoelectric ceramics, such as those of the barium titanate and lead zirconium titanate families, are suitable substrates. These include, for example, LiNbO$_3$; BaTiO$_3$; 95 wt. % BaTiO$_3$/5% GaTiO$_3$; 80 wt. % BaTiO$_3$/12% PbTiO$_3$/8% CaTiO$_3$; PbNb$_2$O$_6$; Na$_{0.5}$K$_{0.5}$NbO$_3$; Pb$_{0.94}$Sr$_{0.06}$(Ti$_{0.48}$Sr$_{0.52}$)O$_3$; and Pb$_{0.94}$(Ti$_{0.48}$Sr$_{0.52}$)O$_3$. In some cases, the substrate may comprise a piezoelectric coating material, such as ZnO or AlN, applied to a non-piezoelectric material, such as silicon. The piezoelectric properties of these and other suitable materials are provided in *CRC Handbook of Materials Science*, Vol. III, Charles T. Lynch, CRC Press: Boca Raton, 198 (1975).

The sensing portion of an acoustic wave device of the invention is the area under the chemoselective layer where the chemoselective layer covers the transducer. The area of the sensing portion of such a device can be on the order of cm$^2$ to μm$^2$.

An optical waveguide chemical sensor consists of a light source, an optical waveguide, a chemoselective film or layer, and a detector to analyze the light after interacting with the layer. The waveguide is used to propagate light to a sensing portion of the device that contains the chemoselective layer.

The light travels towards this coating and interacts with it. If the analyte being detected is present in the layer, the optical characteristics of the light may be altered, and the change is detected by an optically sensitive detector.

Useful optical chemical sensors, commonly referred to as optrodes, typically include light sources such as semiconductor lasers, light-emitting diodes, or halogen lamps; optical waveguides such as fiber optics or planar waveguide substrates; chemoselective layers deposited on the sensing portion of the optrode exposed to an analyte; and detectors for monitoring the optical characteristics of an optrode. Sorption of the analyte to the chemoselective layer modifies the optical characteristics of the optrode, and this is usually detected as a change in refractive index or light intensity at one or more wavelengths of light. Thus, for optical sensors, both optical fibers and optical wave-guides are well-known in the art and useful in the present invention.

Fiber optic waveguides for sensor applications are commonly manufactured from silica glass or quartz as the core of the fiber. Surrounding this core is a cladding material that exhibits a lower refractive index than the core to achieve internal reflectance. Chemoselective layers are typically applied at the distal tip of a fiber optic or along the side of the fiber optic where a portion of the cladding material has been removed.

Planar waveguide optical sensors use planar substrate devices as light guides. The use of a planar waveguide normally involves the use of evanescent wave techniques to take advantage of the large active surface area available. Many of these sensors use the fluorescent properties of a chemoselective layer and are thus called Total Internal Reflection Fluorescence (TIRF) sensors.

Preferably, acoustic wave devices are used as the substrate for the device of the invention. Particularly preferred are SAW devices such as 915 MHz two-port resonators made of ST-cut quartz with aluminum metallization and a thin silicon dioxide overcoat. SAW resonators and oscillator electronics to drive them are commercially available from RFM, Dallas, Tex.

Before applying a coating to form the sensor portion of the device of the invention, the substrate is usually cleaned. The cleaning procedure typically involves rinsing the device in an organic solvent and then subjecting it to plasma cleaning, as is well-known. Optionally, the substrate can be silanized with a material such as diphenyltetramethyldisilazane (DPTMS) by immersing the cleaned substrate surface in liquid DPTMS and then placing the immersed surface into a partially evacuated chamber heated to about 170° C. for about 12 hours. The silanized substrate is then removed and solvent cleaned with, for example, toluene, methanol, chloroform, or a physical or serial combination thereof, before applying the chemically sensitive sensor layer of the device.

The method used for coating the compounds of the invention onto a substrate is not critical, and various coating methods known in the art may be used. Typically, the coating is applied to the substrate in solution, either by dipping, spraying or painting, preferably by an airbrush or spin coating process. Laser deposition techniques may also be used, particularly when coating MEMS devices. The concentration of the compound of the invention in the coating solution should be sufficient to provide the viscosity most appropriate for the selected method of coating, and may easily be determined empirically.

The solvent used, although not critical, should be sufficiently volatile as to facilitate quick and easy removal, but not so volatile as to complicate the handling of the coating solution prior to being deposited on the substrate. Examples of useful organic solvents include, for example, hexane, chloroform, dichloromethane, toluene, xylenes, acetonitrile and tetrahydrofuran. J. W. Grate and R. A. McGill in *Analytical Chemistry*, Vol. 67, No. 21, 4015–19 (1995), the subject of which is hereby incorporated by reference, describe making chemical acoustic wave detectors by applying a thin film to a surface acoustic wave device. The thickness of the chemoselective layer preferably does not exceed that which would reduce the frequency of a chemical sensor operating at 250 megahertz by about 250 kilohertz and, typically, is in the range of about 0.5 nm to 10 microns, preferably in the range of 5 to 500 nm.

The coating may comprise a single layer or multiple layers. With multiple layers, a layer containing the compound of the invention may be combined with at least one other layer that provides pores suitable for physically eliminating some chemical species of large size that are not to be monitored.

The process of sorption plays a key role in the performance of chemical sensors for gas phase analysis. For example, microsensors, which consist of a physical transducer and a selective sorbent layer, sense changes in the physical properties, such as mass, of the sorbent layer on the surface of the transducer, due to the sorption of analyte molecules from the gas phase into the sorbent layer. Coating properties that are known to elicit a detectable SAW sensor response are mass (i.e., as determined by the thickness and density of the coating), elasticity, viscoelasticity, conductivity, and dielectric constant. Changes in these properties can also result in changes in the attenuation (i.e., loss of acoustic power) of the wave. In some situations, monitoring the attenuation may be preferable to monitoring the velocity of a wave. Alternatively, there are some situations where simultaneously monitoring both velocity and attenuation can be useful. In any event, it is the modification of the sensed properties of the sorbent layer, as a result of sorption, that results in the detection of analyte molecules in the gas phase. SAW devices coated with compounds of the invention are capable of detecting mass changes a low as about 100 $pg/mm^2$. The vapor diffusion rate into and out of the polymer film is generally rapid, but does depend upon the thickness of the polymer film.

Sensor selectivity, the ability to detect a chemical species in an environment containing other chemical species, is generally determined by the ability of the coated layer to specifically sorb the species to be detected to the exclusion of almost all others. For most coatings, selectivity is obtained based on providing stronger chemical interactions between the coated layer and the target species than occurs between the layer and species that are not to be detected. The method of selectively detecting the presence of a chemical entity within an environment comprises (a) placing the sensing portion of the device of the invention in the environment and (b) detecting changes in the coated layer of the sensing portion of the device. The environment may be gaseous or liquid.

More than one device may be provided. For example, a plurality of sensor portions could be used in a sensor array with, e.g., associated control devices and software, in a manner similar to conventional procedures employing sensor arrays.

After an initial sensing has taken place, the coated sensor layer can be purged or cleaned by a second stream, allowing the sensing of a new third stream to take place. For example, for liquid sensing applications, water- or acid-base solutions could be used as purging or cleaning solutions, depending upon the species being detected and the nature of the layer. For gas applications, dry nitrogen or clean air could be used as a cleaning stream.

In the devices and methods of the invention, the compounds are good sorbents for basic vapors, such as organophosphorus and nitro-substituted compounds. It is expected that the devices of the invention could weigh about 0.25 to 5 pounds and could, therefore, be easily mounted on a remote or robotic vehicle for automatically detecting toxic chemicals or buried explosives or munitions. Alternatively, such a device would also be useful for remotely detecting explosives vapors emitting from a person intending the destruction of private property and/or personnel, such as, for example, at crowded public places like airports or arenas where terrorist activity may be suspected.

If desired, it is possible to increase the concentration of explosive vapors contained in the area being monitored, i.e., speed up their release from buried or otherwise hidden munitions or explosives, by irradiating the area with electromagnetic radiation. For example, a beam-forming antenna could be employed to direct high frequency to long wavelength microwave radiation at the area suspected of containing buried munitions, such as landmines. This will gently warm the area being checked and increase explosive vapor leakage prior to testing with the device of the invention. Increasing the concentration of vapor in the soil or other environment surrounding a munition will produce a stronger signal following the reaction with the sensor portion of the device of the invention.

The chemoselective, hyperbranched compounds of the invention exhibit high selectivity and sensitivity toward hydrogen bond basic vapors, due to the sensitivity and selectivity of the halogen substituted alcohol or phenol functional groups that are present. The functionalized hyperbranched compounds of the invention also have the advantage of high-yield preparation methods, ready purification, in addition to having an increased availability of functional groups to analytes, as compared with linear polymeric coatings. Moreover, the flexibility in the synthesis of these materials allows one to tailor a wide variety of related chemoselective hyperbranched compounds.

EXAMPLES

Unless otherwise noted, all synthetic procedures were carried out under inert atmosphere using standard Schlenk and vacuum line techniques. Solvents were dried and degassed under an argon atmosphere using appropriate drying agents.

These examples are intended to illustrate the present invention to those skilled in the art and should not be interpreted as limiting the scope of the invention set forth in the claims.

Example 1

Preparation of $[-CH_2-Si(CH=CHCH_2C(CF_3)_2OH)_2-]_n$

To a 500 mL flask containing 2.1 g of Mg chips was added 30 mL of freshly distilled THF. The resulting mixture was cooled to 0° C. and treated with 10 mL (14.65 g) of $ClCH_2SiCl_3$ via syringe. The reaction mixture was stirred at 0° C. for four hours with an additional 60 mL of THF being added in portions as needed to keep the solution from getting too thick due to salt formation. The reaction mixture was then stirred for 2 hours at room temperature and treated dropwise with allylmagnesium bromide (162 mL of 1.0 M in ether) over a two hour period. The resulting solution was stirred at room temperature for 20 hours. The reaction was then quenched with saturated aqueous $NH_4Cl$ and the organic portion extracted with diethyl ether, dried over $MgSO_4$, and filtered through 1 cm of $SiO_2$. Removal of the volatiles left the product polymer as a pale yellow, viscous oil. A sample of the parent polymer (2.0 g) was dissolved in $CHCl_3$ (30 mL) and placed into a mild steel cylinder along with a magnetic stir bar. The steel cylinder was then cooled in liquid nitrogen and evacuated. Hexafluoroacetone (~4.0 g) was introduced into the steel cylinder via vacuum transfer. The cylinder was sealed, removed from the vacuum line, and heated to 65° C. for 48 hours. The cylinder was then cooled to room temperature and the volatiles removed under vacuum. Once evacuated, the reaction cylinder was opened to the air, and the hyperbranched compound inside was extracted with chloroform (4×30 mL). The resulting solution was filtered through Celite and the volatiles removed to give a pale brown polymer. FTIR (NaCl, cm$^{-1}$) showed the characteristic OH stretch (~3510 cm$^{-1}$) verifying the presence of the $-C(CF_3)_2OH$ groups in the functionalized product.

Example 2

Preparation of $[-CH_2-Si\{CH_2CH_2CH_2C_6H_3(C(CF_3)_2OH)_2\}_2]_n$

To a 500 mL flask containing 7.0 g of Mg chips was added 20 mL of freshly distilled THF. The resulting mixture was cooled to 0° C. and treated with 10 mL (14.65 g) of $ClCH_2SiCl_3$ via syringe. The reaction mixture was stirred at 0° C. for four hours with an additional 60 mL of THF being added in portions as needed to keep the solution from getting too thick due to salt formation. The reaction mixture was stirred for 2 hours at room temperature then cooled to 0° C. and treated drop-wise with a THF (60 mL) solution of (3-bromopropyl)benzene (25.5 mL) over a two hour period. The reaction mixture was then allowed to warm with occasional cooling to maintain the temperature below 40° C. The resulting solution was stirred at room temperature for 20 hours. The reaction was then quenched with saturated aqueous $NH_4Cl$ and the organic portion extracted with diethyl ether, dried over $MgSO_4$, and filtered through 1 cm of $SiO_2$. Removal of the volatiles left the product polymer as a pale yellow viscous oil. A sample of the parent polymer (2.0 g) was mixed with a catalytic amount of $AlCl_3$ (0.1 g) and placed into a mild steel cylinder along with a magnetic stir bar. The steel cylinder was then cooled in liquid nitrogen and evacuated. Hexafluoroacetone (~4.0 g) was introduced into the steel cylinder via vacuum transfer. The cylinder was sealed, removed from the vacuum line, and heated to 65° C. for 48 hours. The cylinder was then cooled to room temperature and the volatiles removed under vacuum. Once evacuated, the reaction cylinder was opened to the air, and the hyperbranched compound inside was extracted with chloroform (4×30 mL). The resulting solution was washed with water, dried over $MgSO_4$, filtered through Celite and the volatiles removed to give a pale brown viscous oil. FTIR (NaCl, cm$^{-1}$) showed an OH stretch (~3510 cm$^{-1}$) verifying the presence of the $-C(CF_3)_2OH$ groups in the functionalized product.

Example 3

Preparation of [—CH$_2$—Si{CH$_2$CH=CHC$_6$H$_3$(C(CF$_3$)$_2$OH)$_2$}$_2$]$_n$

To a 500 mL flask containing 7.0 g of Mg chips was added 20 mL of freshly distilled THF. The resulting mixture was cooled to 0° C. and treated with 10 mL (14.65 g) of ClCH$_2$SiCl$_3$ via syringe mixture was stirred at 0° C. for four hours with an additional 60 mL of THF being added in portions as needed to keep the solution from getting too thick due to salt formation. The reaction mixture was stirred for 2 hours at room temperature then cooled to 0° C. and treated dropwise with a THF (60 mL) solution of cinnamyl bromide (33.0 g) over a six hour period. The resulting solution was stirred at room temperature for 20 hours. The reaction was then quenched with saturated aqueous NH$_4$Cl and the organic portion extracted with diethyl ether, dried over MgSO$_4$, and filtered through 1 cm of SiO$_2$. Removal of the volatiles left the product polymer as a yellow, viscous oil. A sample of the parent polymer (2.0 g) was mixed with a catalytic amount of AlCl$_3$ (0.1 g) and placed into a mild steel cylinder along with a magnetic stir bar. The steel cylinder was then cooled in liquid nitrogen and evacuated. Hexafluoroacetone (~4.5 g) was introduced into the steel cylinder via vacuum transfer. The cylinder was sealed, removed from the vacuum line, and heated to 65° C. for 48 hours. The cylinder was then cooled to room temperature and the volatiles removed under vacuum. Once evacuated, the reaction cylinder was opened to the air, and the hyperbranched compound inside was extracted with chloroform (4×30 mL). The resulting solution was washed with water, dried over MgSO$_4$, filtered through Celite and the volatiles removed to give a pale brown viscous oil. FTIR (NaCl, cm$^{-1}$) showed an OH stretch (~3510 cm$^{-1}$) verifying the presence of the —C(CF$_3$)$_2$OH groups in the functionalized product.

Example 4

–Preparation of [—(CH$_2$)$_2$—Si{CH$_2$Si{CH=CHCH$_2$(C(CF$_3$)$_2$OH)}$_3$}$_2$]$_n$ To a 500 mL flask containing 6.0 g of Mg chips was added 20 mL of freshly distilled THF. The resulting mixture was cooled to 0° C. and treated with 10.0 mL (16.69 g) of BrCH$_2$CH$_2$SiCl$_3$ via syringe. The reaction mixture was stirred at 0° C. for four hours with an additional 60 mL of THF being added in portions as needed to keep the solution from getting too thick due to salt formation. The reaction mixture was stirred for 2 hours at room temperature then cooled to 0° C. and treated dropwise with a THF (50 mL) solution of chloromethyl-triallylsilane (26.0 g) over a four hour period. The resulting solution was stirred at room temperature for 24 hours. The reaction was then quenched with saturated aqueous NH$_4$Cl and the organic portion extracted with diethyl ether, dried over MgSO$_4$, and filtered through 1 cm of SiO$_2$. Removal of the volatiles left the product polymer a viscous oil. A sample of the parent polymer (2.0 g) was dissolved in CHCl$_3$ (30 mL) and placed into a mild steel cylinder along with a magnetic stir bar. The steel cylinder was then cooled in liquid nitrogen and evacuated. Hexafluoroacetone (~4.5 g) was introduced into the steel cylinder via vacuum transfer. The cylinder was sealed, removed from the vacuum line, and heated to 65° C. for 48 hours. The cylinder was then cooled to room temperature and the volatiles removed under vacuum. Once evacuated, the reaction cylinder was opened to the air, and the hyperbranched compound inside was extracted with chloroform (4×30 mL). The resulting solution was washed with water, dried over MgSO$_4$, filtered through Celite and the volatiles removed to give a pale brown viscous oil. FTIR (NaCl, cm$^{-1}$) showed an OH stretch (~3510 cm$^{-1}$) verifying the presence of the —C(CF$_3$)$_2$OH groups in the functionalized product.

Example 5

Preparation of [—(CH$_2$)$_3$—Si(CH=CHCH$_2$C(CF$_3$)$_2$OH)$_2$—]$_n$

To a 50 mL flask was added triallylsilane (2.1 g) and tetraallylsilane (0.1 g) along with 1–2 drops of 0.1 mM H$_2$PtCl$_6$(H$_2$O)$_x$ in THF. The resulting mixture was stirred at 50° C. for 18 hours resulting in a viscous pale yellow oil. The reaction mixture was dissolved in 20 mL of hexanes and filtered through 1 cm of SiO$_2$. Removal of the volatiles left the product polymer as a pale yellow, viscous oil. A sample of the parent polymer (1.0 g) was dissolved in CHCl$_3$ (20 mL) and placed into a mild steel cylinder along with a magnetic stir bar. The steel cylinder was then cooled in liquid nitrogen and evacuated. Hexafluoroacetone (~3.0 g) was introduced into the steel cylinder via vacuum transfer. The cylinder was sealed, removed from the vacuum line, and heated to 65° C. for 48 hours. The cylinder was then cooled to room temperature and the volatiles removed under vacuum. Once evacuated, the reaction cylinder was opened to the air, and the hyperbranched compound inside was extracted with chloroform (4×30 mL). The resulting solution was filtered through Celite and the volatiles removed to give a pale brown polymer. FTIR (NaCl, cm$^{-1}$) showed the characteristic OH stretch (~3510 cm$^{-1}$) verifying the presence of the —C(CF$_3$)$_2$OH groups in the functionalized product.

Example 6

Preparation of [—(CH$_2$)$_3$—Si(CH$_2$CH$_2$CH$_2$C$_6$H$_3$(C(CF$_3$)$_2$OH)$_2$) (CH=CHCH$_2$C(CF$_3$)$_2$OH)—]$_n$ To a 50 mL flask was added 3-phenylpropyldiallylsilane (3.1 g) and allylbenzene (0.05 g) along with 1–2 drops of 0.1 mM H$_2$PtCl$_6$(H$_2$O)$_x$ in THF. The resulting mixture was stirred at 50° C. for 22 hours resulting in a viscous pale yellow oil. The reaction mixture was dissolved in 20 mL of hexanes and filtered through 1 cm of SiO$_2$. Removal of the volatiles left the product polymer as a pale yellow, viscous oil. A sample of the parent polymer (1.5 g) was dissolved in CHCl$_3$ (30 mL) and placed into a mild steel cylinder along with a magnetic stir bar. The steel cylinder was then cooled in liquid nitrogen and evacuated. Hexafluoroacetone (~3.5 g) was introduced into the steel cylinder via vacuum transfer. The cylinder was sealed, removed from the vacuum line, and heated to 65° C. for 48 hours. The cylinder was then cooled to room temperature and the volatiles removed under vacuum. Once evacuated, the reaction cylinder was opened to the air, and the hyperbranched compound inside was extracted with chloroform (4×30 mL). The resulting solution was filtered through Celite and the volatiles removed to give a pale brown polymer. FTIR (NaCl, cm$^{-1}$) showed the characteristic OH stretch (~3510 cm$^{-1}$) verifying the presence of the —C(CF$_3$)$_2$OH groups in the functionalized product.

Example 7

Preparation of co—[—(CH$_2$)$_3$—Si(CH$_2$CH$_2$CH$_2$C$_6$H$_3$(C(CF$_3$)$_2$OH)$_2$)—]$_m$—[—(CH$_2$)$_3$Si(CH═CHCH$_2$C—(CF$_3$)$_2$OH)$_2$—]$_n$ To a 50 mL flask was added 3-phenylpropyldiallylsilane (1.8 g), triallylsilane (2.5 g) and tetraallylsilane (0.1 g) along with 1–2 drops of 0.1 mM H$_2$PtCl$_6$(H$_2$O)$_x$ in THF. The resulting mixture was stirred at 50° C. for 20 hours resulting in a viscous pale yellow oil. The reaction mixture was dissolved in 20 mL of hexanes and filtered through 1 cm of SiO$_2$. Removal of the volatiles left the product polymer as a pale yellow, viscous oil. A sample of the parent polymer (1.5 g) was dissolved in CHCl$_3$ (30 mL) and placed into a mild steel cylinder along with a magnetic stir bar. The steel cylinder was then cooled in liquid nitrogen and evacuated. Hexafluoroacetone (~4.0 g) was introduced into the steel cylinder via vacuum transfer. The cylinder was sealed, removed from the vacuum line, and heated to 65° C. for 48 hours. The cylinder was then cooled to room temperature and the volatiles removed under vacuum. Once evacuated, the reaction cylinder was opened to the air, and the hyperbranched compound inside was extracted with chloroform (4×30 mL). The resulting solution was filtered through Celite and the volatiles removed to give a pale brown polymer. FTIR (NaCl, cm$^{-1}$) showed the characteristic OH stretch (~3510 cm$^{-1}$) verifying the presence of the —C(CF$_3$)$_2$OH groups in the functionalized product.

Example 8

Preparation of co—[Si{CH$_2$CH$_2$CH$_2$Si(CH$_2$CH$_2$CH$_2$C$_6$H$_3$(C(CF$_3$)$_2$OH)$_2$)[CH$_2$CH$_2$CH$_2$Si(CH$_2$CH$_2$CH$_2$C$_6$H$_3$(C(CF$_3$)$_2$OH)$_2$)(CH═CHCH$_2$C(CF$_3$)$_2$OH)$_{2-x}$(CH$_2$CH$_2$CH$_2$)$_x$—]$_2$}$_4$]—[—(CH$_2$)$_3$—Si(CH═CHCH$_2$C(CF$_3$)$_2$OH)$_2$—]$_n$ To a 100 mL flask was added triallylsilane (2.5 g) and the dendrimeric polymer Si{CH$_2$CH$_2$CH$_2$Si(CH$_2$CH$_2$CH$_2$C$_6$H$_5$)[CH$_2$CH$_2$CH$_2$Si(CH$_2$CH$_2$CH$_2$C$_6$H$_5$)(CH$_2$CH═CH$_2$)$_2$]$_2$}$_4$ (0.20 g) along with 1–2 drops of 0.1 mM H$_2$PtCl$_6$(H$_2$O)$_x$ in THF. The resulting mixture was stirred at 50° C. for 24 hours resulting in a viscous pale yellow oil. The reaction mixture was dissolved in 20 mL of hexanes and filtered through 1 cm of SiO$_2$. Removal of the volatiles left the product polymer as a pale yellow, viscous oil. A sample of the parent polymer (1.0 g) was dissolved in CHCl$_3$ (30 mL) and placed into a mild steel cylinder along with a magnetic stir bar. The steel cylinder was then cooled in liquid nitrogen and evacuated. Hexafluoroacetone (~3.0 g) was introduced into the steel cylinder via vacuum transfer. The cylinder was sealed, removed from the vacuum line, and heated to 65° C. for 48 hours. The cylinder was then cooled to room temperature and the volatiles removed under vacuum. Once evacuated, the reaction cylinder was opened to the air, and the hyperbranched compound inside was extracted with chloroform (4×30 mL). The resulting solution was filtered through Celite and the volatiles removed to give a pale brown polymer. FTIR (NaCl, cm$^{-1}$) showed the characteristic OH stretch (~3510 cm$^{-1}$) verifying the presence of the —C(CF$_3$)$_2$OH groups in the functionalized product.

Example 9

Preparation of co—[—(CH$_2$)$_3$—Si(Me)O—]$_m$—[—(CH$_2$)$_3$—Si(CH═CHCH$_2$C(CF$_3$)$_2$OH)$_2$—]$_n$ To a 100 mL flask was added triallylsilane (3.0 g), tetraallylsilane (0.05 g) and poly(methylhydridosiloxane) (0.15 g) along with 1–2 drops of 0.1 mM H$_2$PtCl$_6$(H$_2$O)$_x$ in THF. The resulting mixture was stirred at 50° C. for 24 hours resulting in a viscous pale yellow oil. The reaction mixture was dissolved in 20 mL of hexanes and filtered through 1 cm of SiO$_2$. Removal of the volatiles left the product polymer as a pale yellow, viscous oil. A sample of the parent polymer (1.0 g) was dissolved in CHCl$_3$ (30 mL) and placed into a mild steel cylinder along with a magnetic stir bar. The steel cylinder was then cooled in liquid nitrogen and evacuated. Hexafluoroacetone (~3.0 g) was introduced into the steel cylinder via vacuum transfer. The cylinder was sealed, removed from the vacuum line, and heated to 65° C. for 48 hours. The cylinder was then cooled to room temperature and the volatiles removed under vacuum. Once evacuated, the reaction cylinder was opened to the air, and the hyperbranched compound inside was extracted with chloroform (4×30 mL). The resulting solution was filtered through Celite and the volatiles removed to give a pale brown polymer. FTIR (NaCl, cm$^{-1}$) showed the characteristic OH stretch (~3510 cm$^{-1}$) verifying the presence of the —C(CF$_3$)$_2$OH groups in the functionalized product.

Example 10

Applying a Thin Film to a SAW Device

SAW devices are cleaned in a Harrick plasma cleaner prior to polymer film application. Spray-coated films of the compound of FIG. 1 in chloroform (1% by weight) are applied to a SAW device using an airbrush supplied with compressed dry nitrogen. The frequency change of the SAW device operating in an oscillator circuit is monitored during deposition, using the change in frequency, typically about 250 kHz, as a measure of the amount of material applied. After application, the films are optionally annealed in an oven at 50° C. overnight. Spray-coated films are examined by optical microscopy with a Nikon microscope using reflected light Nomarski differential interference contrast.

Example 11

Detection of Basic Vapors with a Compound-Coated SAW Device

The compounds of FIGS. 1 and 2 are separately applied to SAW devices and tested against organic vapors at various concentrations. Upon exposure to a vapor, the coated acoustic wave devices undergo a shift in frequency that is proportional to the concentration of the vapor. Times to steady state response, corresponding to equilibrium partitioning of the vapor into the compound layer, are typically under 10 seconds using a vapor delivery system. From frequency shift data for a vapor at multiple concentrations, calibration curves are constructed. The calibration curves are generally linear at moderate concentrations, but deviate from linearity at the high and low concentration levels. Linear calibration curves are consistent with hydrogen-bonding interactions at a finite number of sites in the compound.

Example 12

Coating a Capillary Column

A solution of the compound of FIG. 2 in chloroform is used to coat the interior surface of several one-meter silica capillary columns with an inside diameter of 100 microns. The procedure to coat a 100-micron i.d. column from Fused Silica Intermediate Polarity (part number 2-5745, Supelco, Pennsylvania) involves filling the capillary with a solution of the compound, closing one end of the capillary, and pulling a vacuum off the other end of the capillary at a fixed temperature. The solution-filled column is placed into a gas chromatographic oven stabilized at 30° C. to control the temperature. A vacuum is then pulled using an oil-free Teflon-coated diaphragm pump (Fisher part number 13-875-217C), with a vacuum of −70 kPa, typically being applied for about 15–20 hours.

The thickness and thickness uniformity are verified by cutting a coated column into several pieces and looking at the cross sections using a high power optical microscope. The thickness of one micron is usually in good agreement with the theoretical film thicknesses.

Example 13

Optical Fiber Drawing and Cladding

The compound of FIG. 2 is combined with a solvent to form a viscous mixture, which is stirred until well-blended and degassed under vacuum. The viscous mixture is applied to a fused silica fiber as it is freshly drawn from a Heathway fiber drawing apparatus through a 2–5 mm Sandcliff cladding cup, and into a 45 cm long clamshell furnace for curing. The viscous mixture is supplied to the cladding cup under a pressure of about 0.8 to about 1.5 psi. The optimal furnace temperature and fiber draw-speed are typically about 520° C. and 8–9 m/min, respectively. These relatively slow draw rates are usually used for manual control of the drawing conditions, but sometimes result in variable core diameters and coating thickness. However, when used with the other conditions described, a fairly uniform coating that is light yellow in color and slightly tacky to the touch is usually obtained. As the viscosity of the solution of the compound increases during the fiber drawing, the delivery pressure should be increased over the course of filling, usually about two hours.

Half-meter to one-meter sections are hand selected for quality. The best fiber sections made under these conditions have a smooth coating of about 25 microns thick over a 180-micron diameter core. All are usually effective in guiding light.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A polymeric compound having:
   (1) a polymer backbone portion that is at least partly branched;
   (2) at least one pendant arm extending from said polymer backbone; and
   (3) at least one halogen substituted alcohol or phenol group substituted at the pendant group(s) of the polymer backbone portion;
   wherein said compound has the general formula:

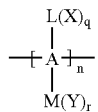

wherein A is the backbone portion of the polymer and is —Si—(CH$_2$)$_n$— wherein n=1;
   L is C$_3$H$_4$ and M is C$_3$H$_4$;
   X is hexafluoroisopropanol and Y is hexafluoroisopropanol; and
   q and r are independently selected and q is 1 and r is 1 and n is at least 3.

2. A solution for preparing a chemical vapor sensor comprising:
   (a) an amount of a compound having
      (1) a polymer backbone portion that is at least partly branched;
      (2) at least one pendant group extending from the polymer backbone portion;
      (3) at least one halogen substituted alcohol or phenol group substituted at the pendant group(s) of the polymer backbone portion, effective to enhance the sensitivity of the sensor to hydrogen bond accepting vapors or nitroaromatic compounds; and
   (b) a solvent for said compound wherein said compound has the general formula:

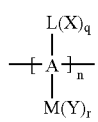

wherein A is the backbone portion of the polymer and is —Si—(CH$_2$)$_n$— wherein n=1;
   L is C$_3$H$_4$ and M is C$_3$H$_4$;
   X is hexafluoroisopropanol and Y is hexafluoroisopropanol; and
   q and r are independently selected and q is 1 and r is 1 and n is at least 3.

3. The solution of claim 2 wherein said solvent is selected from the group consisting of hexane, chloroform, dichloromethane, toluene, xylenes, acetonitrile and tetrahydrofuran.

* * * * *